United States Patent
Henriksen

(12) 
(10) Patent No.: US 10,064,550 B2
(45) Date of Patent: Sep. 4, 2018

(54) METHOD AND APPARATUS FOR OBTAINING AN IMAGE OF AN OCULAR FEATURE

(75) Inventor: David R. Henriksen, Fort Collins, CO (US)

(73) Assignee: OPTIBRAND LTD., LLC, Ft. Collins, CO (US)

( * ) Notice: Subject to any disclaimer, the term of this patent is extended or adjusted under 35 U.S.C. 154(b) by 1144 days.

(21) Appl. No.: 13/119,604

(22) PCT Filed: Oct. 15, 2008

(86) PCT No.: PCT/US2008/080028
§ 371 (c)(1),
(2), (4) Date: Mar. 17, 2011

(87) PCT Pub. No.: WO2010/044791
PCT Pub. Date: Apr. 22, 2010

(65) Prior Publication Data
US 2011/0169935 A1 Jul. 14, 2011

(51) Int. Cl.
| H04N 9/47 | (2006.01) |
| A61B 3/12 | (2006.01) |
| G06T 7/00 | (2017.01) |

(52) U.S. Cl.
CPC .............. *A61B 3/12* (2013.01); *G06T 7/0012* (2013.01); *G06T 2207/10016* (2013.01); *G06T 2207/10152* (2013.01); *G06T 2207/30041* (2013.01)

(58) Field of Classification Search
USPC .......................................... 348/78, E07.085
See application file for complete search history.

(56) References Cited

U.S. PATENT DOCUMENTS

| 6,289,113 B1 | 9/2001 | McHugh | |
| 6,523,954 B1 * | 2/2003 | Kennedy et al. | 351/205 |

(Continued)

FOREIGN PATENT DOCUMENTS

| CN | 101172035 | 5/2008 |
| JP | 2001-017411 | 1/2001 |

(Continued)

OTHER PUBLICATIONS

International Search Report and Written Opinion dated Jun. 22, 2009 for International Application No. PCT/US08/80028.

(Continued)

*Primary Examiner* — Christopher S Kelley
*Assistant Examiner* — Ana Picon-Feliciano
(74) *Attorney, Agent, or Firm* — Swanson & Bratschun, L.L.C.

(57) ABSTRACT

A method, apparatus and software containing instructions for obtaining an image of an ocular feature are disclosed. The disclosed embodiments include at least the steps of defining one or more selection criteria which are related to an ocular feature of interest. The selection criteria may relate to an ocular feature type, an ocular feature location, or other relevant matters. The method further includes capturing a stream of sequential ocular images and autonomously scoring some or all ocular images according to the selection criteria. Images that score above a defined score threshold may be selected as individual images more likely to include a suitable representation of the ocular feature of interest than other individual ocular images.

20 Claims, 7 Drawing Sheets

(56) References Cited

U.S. PATENT DOCUMENTS

| | | | |
|---|---|---|---|
| 2004/0085514 A1* | 5/2004 | Fransen | 351/206 |
| 2004/0105075 A1* | 6/2004 | Kandel et al. | 351/221 |
| 2004/0169817 A1* | 9/2004 | Grotehusmann et al. | 351/204 |
| 2005/0057721 A1* | 3/2005 | Kolanko et al. | 351/205 |
| 2005/0094102 A1* | 5/2005 | Cornsweet et al. | 351/221 |
| 2005/0270489 A1* | 12/2005 | Michelson et al. | 351/246 |
| 2006/0181678 A1* | 8/2006 | Stark et al. | 351/206 |
| 2008/0100801 A1 | 5/2008 | Yahagi | |
| 2008/0199165 A1* | 8/2008 | Ng et al. | 396/51 |
| 2008/0204655 A1* | 8/2008 | Kikawa et al. | 351/206 |
| 2008/0212026 A1* | 9/2008 | Molnar et al. | 351/206 |

FOREIGN PATENT DOCUMENTS

| | | |
|---|---|---|
| JP | 2006-122647 | 5/2006 |
| WO | WO 02/076334 | 10/2002 |
| WO | WO 03/020112 | 3/2003 |
| WO | WO 03020112 A2 * | 3/2003 |
| WO | WO 2008/091401 | 7/2008 |

OTHER PUBLICATIONS

International Preliminary Report on Patentability dated Apr. 19, 2011 for International Application No. PCT/US08/80028.

European extended Search Report dated Jul. 24, 2014 for Corresponding EP Application No. 08877466.6.

Belcher and Du, 2008, IEEE Transactions on Information Forensics and Security 3(3): 572-577, "A Selective Feature Information Approach for Iris Image-Quality Measure".

Pansing et al., 2005, SPIE Proceedings v5875, "Optimization of illumination schemes in a head-mounted display integrated with eye tracking capabilities".

* cited by examiner

METHOD AND APPARATUS FOR OBTAINING AN IMAGE OF AN OCULAR FEATURE

RELATED APPLICATIONS

This application is a 35 U.S.C. § 371 national phase application of PCT/US08/80028 (WO 2010/044791), filed on Oct. 15, 2008, entitled "Method and Apparatus for Obtaining an Image of an Ocular Feature", which is incorporated herein by reference in its entirety.

TECHNICAL FIELD

The embodiments disclosed herein are directed toward methods and apparatus for obtaining an image of an ocular feature, in particular methods and apparatus configured to capture a suitable ocular feature image where the subject eye may be moving, or is not artificially dilated.

BACKGROUND

It is often desirable to capture a digital image of an ocular feature for many medical or veterinary purposes. As used herein, an ocular feature is defined as any anatomical structure associated with an animal or human eye. For example, an ocular feature may include, but is not limited to, the retina, optic nerve or the retinal vascularization of an animal or human subject's eye. Digital images of an ocular feature may be useful to assist with the diagnosis of a condition, abnormality, disease, or healthy eye. Similarly a series of images of an ocular feature taken over time may be utilized to track the progression of a condition, abnormality, disease or healthy eye.

The capture of digital images of ocular features may be both difficult and time consuming, particularly when the subject of examination is unable to keep from moving their eye for any reason. For example, animals are typically unwilling or unable to hold their eyes still for veterinary examination. Babies and children may find it impossible or difficult to hold their eyes still during an examination as well. Premature babies have an increased risk of developing retinopathy. Because of this, multiple retinal eye exams are routinely performed on premature babies during the first several months after birth. Typically, a retinal examination is a very challenging and invasive procedure to perform on a newborn since babies generally move their eyes around very rapidly making it difficult for an ophthalmologist to get a clear view of the retina. In addition, the field of view of many optical fundus cameras is relatively small when compared to the entire inner structure of any eye. Thus, it is very difficult for an examining ophthalmologist to capture a suitable image that shows a particular ocular feature or region of interest within the eye to aid in the diagnosis of a condition, disease or abnormality as described above.

It is also often desirable to capture a high quality digital image of an ocular feature without the use of medication to fully dilate the patient's pupil. For example, it is often deemed prudent to avoid using medication to dilate the patient's pupil when the patient is an animal or a baby. High quality ocular imaging, however, requires a significant amount of light to fully illuminate the ocular feature of interest. The application of sufficient illumination to a patient's non-medicated eye for high resolution imaging will typically cause a rapid pupil response significantly reducing the area through which interior ocular features may be viewed and thus limiting the available field of view. Pupil constriction will also dramatically reduce the penetration of the light used to image the feature.

The present embodiments are directed toward overcoming one or more of the problems noted above.

SUMMARY OF THE EMBODIMENTS

Figure 1:
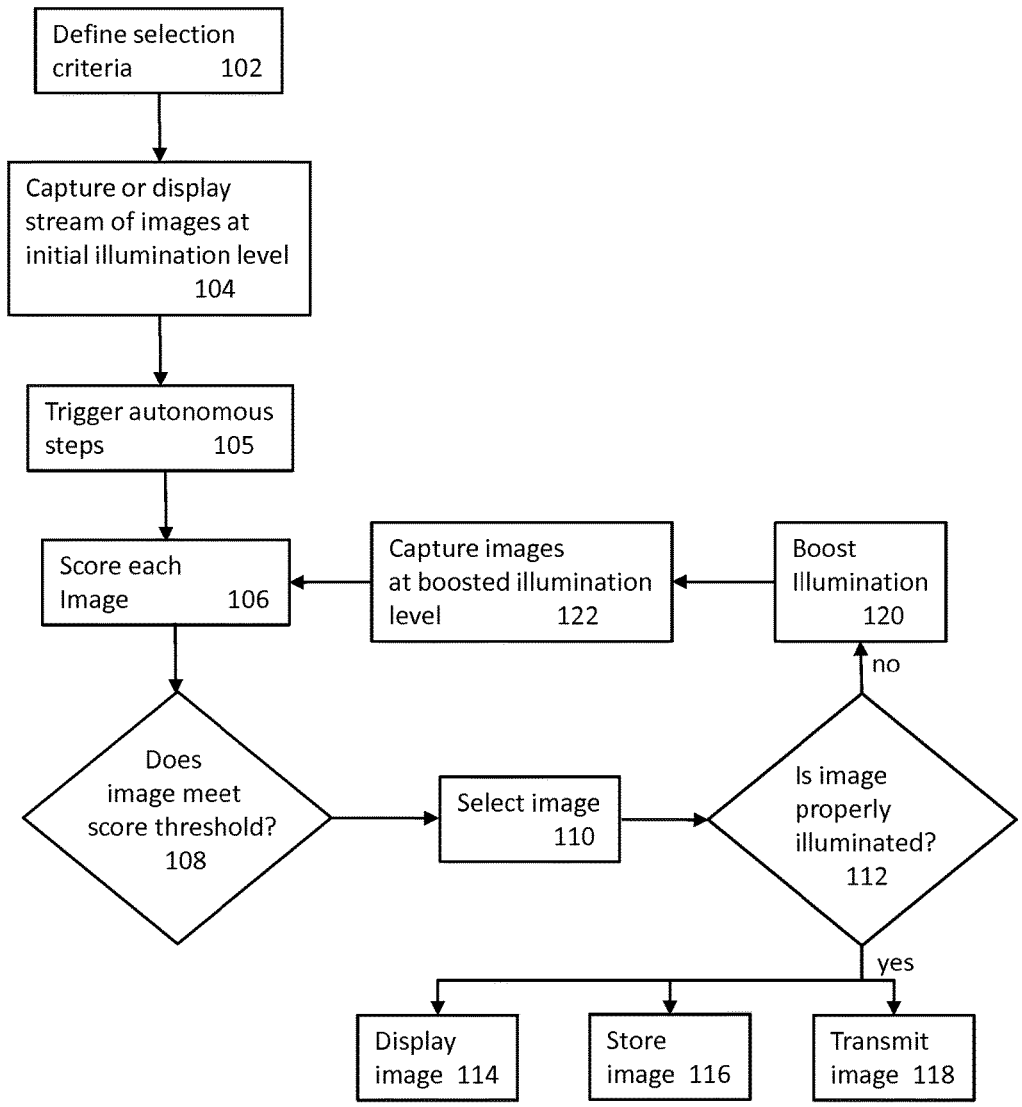
FIG. 1 is a flowchart representation of a disclosed method.

One embodiment is a method of obtaining an image of an ocular feature. The method includes at least the steps of defining one or more selection criteria which are related to an ocular feature of interest. The selection criteria may relate to an ocular feature type, an ocular feature location, or other relevant matters. The method further includes capturing a stream of sequential ocular images and autonomously scoring some or all ocular images according to the selection criteria. Images that score above a defined score threshold may be selected as individual images more likely to include a suitable representation of the ocular feature of interest than other individual ocular images.

When one or more suitable ocular images are selected as described above, the images may be displayed, stored or electronically transmitted to another user or database. The initial stream of sequential ocular images may be captured at an initial illumination level which may be selected to minimize pupil constriction of the subject eye. Subsequently, a second illumination level may be applied while capturing a second segment of the stream of sequential ocular images. The second illumination level is typically of higher intensity than the initial illumination level. The second illumination level may be autonomously provided when an individual ocular image is selected which exceeds the score threshold. The second illumination level may be applied for a period of time which is related to the anticipated pupil constriction response time of the subject eye.

The disclosed methods will include a scoring step as described above. Any selected ocular image may be scored by autonomously detecting the presence of the desired ocular feature or by determining an ocular feature location with respect to the general eye anatomy. Known image analysis and feature detection algorithms may be used to implement autonomous scoring. The scoring process may also include an autonomous determination of general image quality.

Another embodiment is an apparatus for obtaining an image of an ocular feature. The apparatus will include a digital camera suitable for taking a stream of sequential ocular images and a processor running software or firmware configured to accept image data and autonomously score each ocular image according to pre-determined selection criteria. The apparatus may also include a display for displaying a selected image, a data storage device for storing image data or a communications interface for electronically transmitting at least one image.

The apparatus may further include a variable illumination source which can be configured to provide an initial illumination level while capturing initial images and a second, higher illumination level when triggered.

The methods described herein may be implemented in large part through an autonomous, software or firmware controlled process. Another embodiment disclosed herein includes a computer readable medium having executable instructions for performing the described methods.

DETAILED DESCRIPTION OF THE EMBODIMENTS

The embodiments disclosed herein include methods, apparatus and computer readable medium containing instructions for executing a method of imaging an ocular feature. As used herein, an ocular feature is defined as any anatomical structure, portion, surface or region of an eye. For example, representative ocular features include, but are not limited to, the retina, the optic nerve, retinal vasculature and similar structures. The methods and apparatus disclosed herein may be used to obtain an image of an animal eye or a human eye. The images obtained may be used for any suitable purpose including, but not limited to, the diagnosis of an abnormality, condition, disease or healthy ocular feature and the monitoring of same over time.

The methods and apparatus disclosed herein are particularly useful for obtaining one or more high quality images of an ocular feature in situations where the patient is unable to hold their eye absolutely steady. For example, animals, babies and children are typically unable to hold their eye still for ocular examination. Thus, focusing on and imaging a feature with a diagnostic camera that may have a relatively limited field of view becomes a matter of trial and error. In addition, the methods and apparatus disclosed herein are well suited for capturing a high quality image of an ocular feature where the ophthalmologist, veterinarian, or other suitably trained person using the camera can not or chooses not to use medication to dilate the patient's pupil before obtaining an image. Accordingly, methods are disclosed herein for capturing images at multiple illumination levels where typically at least one illumination level is selected to be low enough to avoid causing substantial pupil constriction.

As detailed below the methods and apparatus described herein utilize a stream of sequentially captured individual ocular images such as can be captured with a digital video camera, web camera, or other digital apparatus which may or may not be specifically configured for use as an ophthalmologic examination camera. The embodiments disclosed herein may be implemented with any suitable digital capture device.

FIG. 1 is a flowchart diagram illustrating selected steps of a method for obtaining an image of an optical feature consistent with the embodiments disclosed herein. As shown on FIG. 1, a camera operator may define at least one selection criteria related to the anatomical ocular feature of interest (step 102). The definition of selection criteria will typically be done before any images are captured. Selection criteria may be defined in any manner but are typically stored in software associated with the diagnostic camera. For example, selection criteria may include, but are not limited to, a desired ocular feature type or a desired ocular feature location with respect to the overall anatomy of an eye. Similarly, the selection criteria may require that a certain number of multiple features, for example blood vessels, be included in an image which meets the selection criteria with or without regard to feature location. Selection criteria may also include non-anatomical aspects, for example, illumination level, histogram data, proper focus data, image sharpness and other criteria. After one or more appropriate selection criteria are defined the operator may proceed to capture a stream of images (step 104). The stream of images will typically be captured with a specialized ocular examination camera; however, the stream of images could be captured with any digital video camera which is configured to capture a stream of individual digital images over time.

In one embodiment of the method, the stream of images is captured at an initial illumination level (step 104). The initial illumination level may be selected to avoid stimulating the dramatic constriction of the subject's pupil as is typically observed when a strong illumination source is focused into a subject's eye. The use of a relatively low initial illumination level may result in a less than desired image quality. For example, the images captured at a relatively low initial illumination level may be dark, unsharp, or otherwise of less than the highest quality. However, images captured at an initial illumination level may be adequate for the initiation of subsequent steps which result in a higher quality final image as described below.

As described above, the diagnostic camera used to implement the disclosed methods will be configured to capture a stream of individual digital images over a period of time and at a select capture rate. Although the lenses and other optical components utilized to focus within a patient's eye may be highly specialized, the digital capture mechanism may be implemented with sensor chips and associated electronics such as are commonly used for webcams or digital video cameras. The output from the diagnostic camera may thus be readily displayed in real time on a monitor as a video stream or as periodically selected individual images. This functionality is useful to assist a camera operator with initial camera placement and the initial location of an ocular feature of interest for imaging. For example, since the stream of individual images may be displayed as video, the camera operator may initially manipulate the relatively narrow field camera around the eye while observing video or still image output to generally locate the ocular feature of interest. Accordingly, if the camera operator desires to image the optic nerve root, he or she may manipulate the camera while observing initial output on a monitor to generally assess the location of the optical nerve root. The initial positioning adjustments are optional.

However, if these steps are employed, the operator may trigger subsequent steps in the capture method by depressing a switch or otherwise indicating that initial positioning steps have been completed (step 105).

Upon triggering the camera in step 105, each image in the stream of sequential ocular images may be autonomously scored with respect to the selection criteria by a processor associated with the camera (step 106). Typically the processor will be an outboard processor implemented with an external processing unit such as a computer. Alternatively, the processor utilized to score each image may, if desired, be housed within the camera housing which executes onboard software or firmware for the scoring processes. The scoring process may be used to determine if any individual image in the image stream meets a threshold score with respect to the selection criteria (step 108). The actual scoring process may be implemented with any known image analysis algorithm including, but not limited to, various feature or edge detection methods such as the Canny or Canny-Deriche methods, corner detection methods such as the Harris operator or Shi and Tomasi methods, blob detection methods such as the Laplacian of Gaussian or Difference of Gaussian methods or any other known image analysis and detection method. The image scoring process may include determining if one or more ocular features of the specified type are present in the image and if the image covers the desired feature location. Typically, the scoring process will include comparing data extracted from the selected image by a method similar to those listed above with stored data representative of the feature of interest. Thus, the image scoring step may autonomously determine if the specified ocular feature or type is present in the image and if present, its location within the image. A more specific discussion of one possible implementation of a scoring process is described in detail below.

Scoring each image as described above is particularly useful where a combination of factors associated with the patient and limitations on the optical capabilities of the camera combine to make it unlikely that any individual image selected at random from the image stream is likely to properly show the ocular feature of interest. For example, babies, children and animals will typically move their eye or head around quite a bit during an ocular examination. Therefore, even a highly skilled operator may have a difficult time keeping the camera focused on a region or structure of interest, particularly if the camera has a relatively narrow field of view with respect to the entire eye structure. The method described herein features the capture of many hundreds or thousands of sequential images over a reasonable period of time. Each image is scored in step 106 until one or more images which meet a pre-determined score threshold indicative of the presence of the ocular feature of interest are captured. Thus, the methods described herein substantially reduce the problems associated with subject eye movement and a camera having a relatively narrow field of view.

If a particular image does not meet the selected threshold score, the next image in the stream of images may be scored. When a selected image does meet the selected threshold score (step 108) that image may be selected by the software associated with the processor (step 110). The relative brightness or illumination of the selected image may have been determined in the scoring step 106 as described above. Alternatively, a supplemental determination of the relative brightness of a selected image may be made when the image is selected (step 112). If the selected image is suitably well illuminated the image may be displayed (step 114), stored in memory or storage (step 116) or digitally transmitted through a communications interface or port (step 118). Alternatively, if the selected image is not sufficiently well illuminated to properly show all ocular features of interest the camera illumination output may be boosted for a selected duration (step 120). The duration of the illumination boost will typically correspond to an anticipated pupil reaction time, which is known or may be determined to be appropriate for the subject eye. For example, if a subject has a known delay between the application of high illumination and a significant pupil restriction response of 0.25 second, the illumination may be boosted for 0.25 or less second. After the illumination is boosted, a series of subsequent images may be captured at the boosted illumination level (step 122). Images captured during this second segment of the stream of sequential ocular images may be scored and processed as described above and shown on FIG. 1 in steps 106-118.

It is important to note that the illumination boost of step 120 may be triggered automatically by the capture of an image which meets the score threshold. As described above, this image which meets the score threshold is more likely than previous images to include the ocular feature of interest. Since the software associated with the camera processor may immediately boost illumination levels upon the capture of an image which meets the score threshold, the subsequent highly illuminated images are more likely to include the ocular feature of interest as they will be captured before the subject has a chance to move their eye and before a substantial pupil constriction response.

Various methods may be used to control boosted illumination time relative to lower level illumination time. For example, the software may be configured to count frames at the boosted illumination level. This data when correlated with the frame capture rate can be used to assure that boosted illumination is withdrawn when or before a substantial pupil constriction response is expected. As described above, images captured during a boosted illumination segment of the image stream are both more likely to include the ocular feature of interest and more likely to be of higher quality image because of the use of enhanced illumination levels. These images may be scored as described above and displayed, stored or transmitted assuming that selected images meet or exceed the threshold score.

Figure 2A:
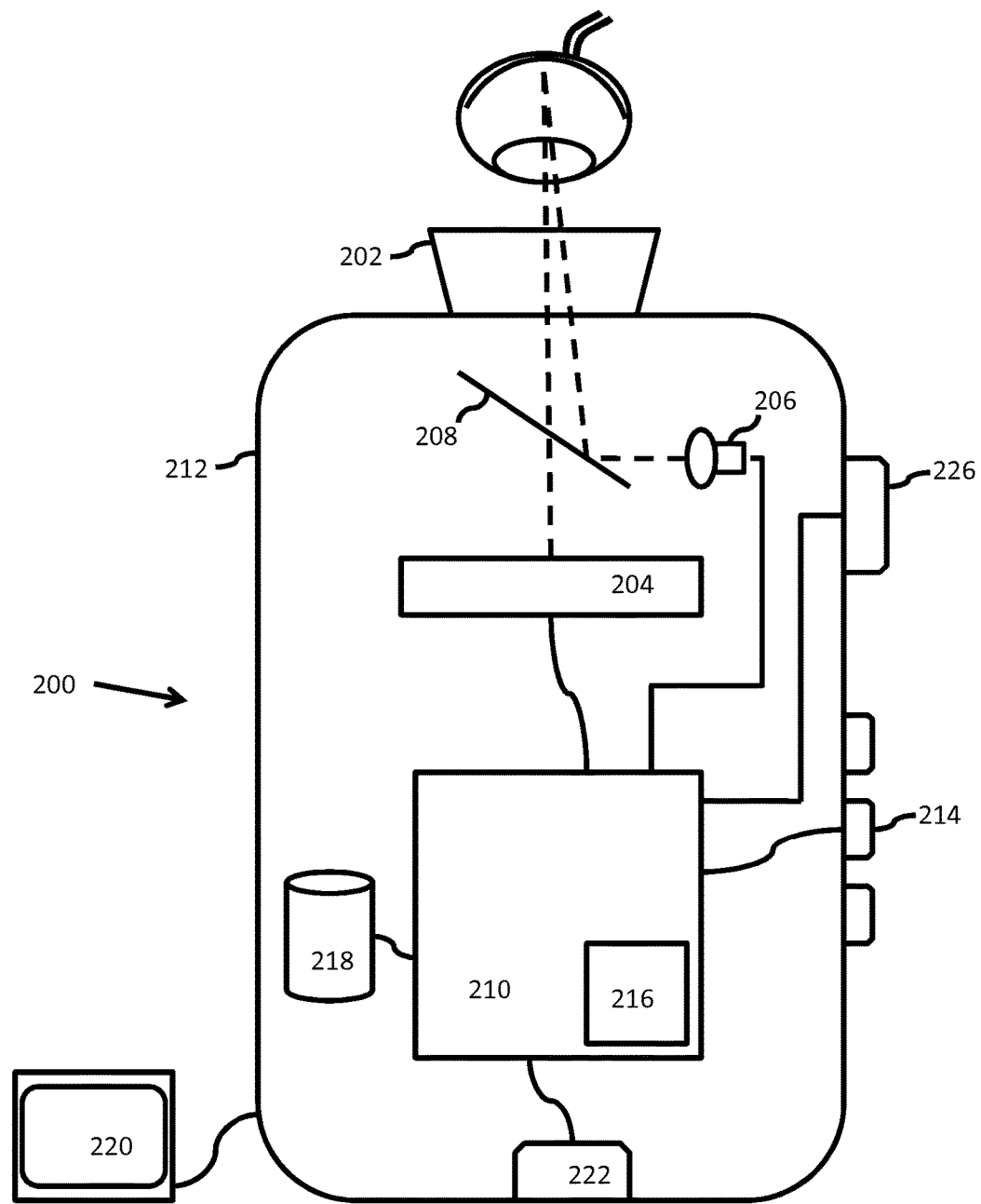
FIG. 2A is a schematic diagram representation of a disclosure apparatus.

The generalized method described above with respect to FIG. 1 may be implemented with many types of suitable diagnostic camera and processing apparatus. FIG. 2A is a schematic diagram of one non-limiting example of a camera 200 suitable for implementing the disclosed methods. The camera 200 includes a lens 202 or other optical elements suitable for focusing illumination light into a subject's eye and focusing a reflected image of an ocular feature onto a digital sensor 204. Illumination may be provided from an illumination source 206 and directed through the lens 202 and into the subject's eye by a beam splitter 208, mirror, prism or similar optical component. Alternatively, illumination may be provided directly through the imaging lens system, remotely from a separate apparatus or otherwise.

Figure 2B:
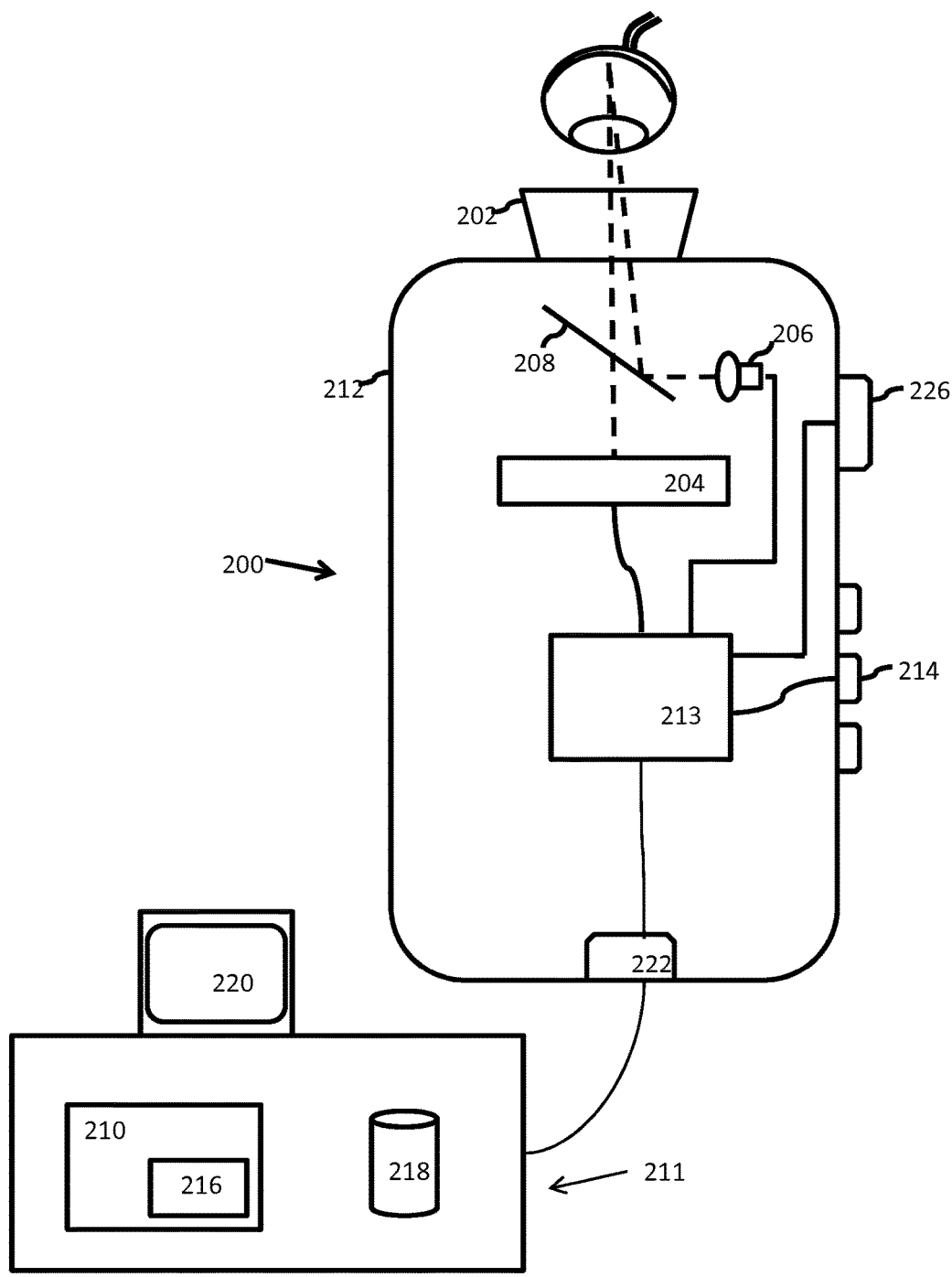
FIG. 2B is a schematic diagram of an alternative apparatus embodiment.

The camera 200 may also include a processor 210. The processor may be included within the camera housing 212 which would facilitate convenient portable use of the apparatus. Alternatively, as shown in FIG. 2B, the processor 210 could be associated with an outboard data processing unit such as a computer 211 which is linked to the camera 200 through a USB port, wireless connection or other means. As shown in FIG. 2B a camera which does not include an onboard processor 210 will still include an onboard video processor 213 as is typically associated with a digital camera board. The video processor 213 is placed in digital communication with the sensor 204 such that any image formed on the sensor 204 is digitized and communicated as image data to the processor 210. In the processor 210, the various scoring steps described above may occur substantially simultaneously with the capture of images presented for processing.

The processor may also be placed in digital communication with one or more input devices 214. The input devices may be, but are not limited to, generally known digital input devices such as keypads, buttons, switches, touchpads, stylus pads, a voice recognition port, a USB or other data link or other known input devices. The input device 214 may be used to input, download or otherwise define at least one selection criteria which may be stored in memory 216 associated with the processor 210. As described above, the stored selection criteria may be used to score each received image. The processor 210 may also be in digital communication with a supplemental onboard or offboard magnetic or optical data storage device 218 such as random access memory (RAM) or various types of flash memory. Similarly, the processor 210 may be digitally linked to a display 220 such as a computer monitor or a communication port 222 for example, a modem or USB port.

As described above, it may be advantageous in certain situations to preview images before the specific scoring and capture algorithms are engaged. For example, a camera technician may desire to generally or roughly point and focus the camera at a location or ocular feature. After initial positioning, the operator may engage the autonomous image scoring, light boosting, and display or storage steps by depressing a switch or trigger 226. Although the monitor element 220 of FIG. 2 is shown as an outboard computer monitor it is important to note that a monitor could be associated with the camera housing 212.

Figure 3:
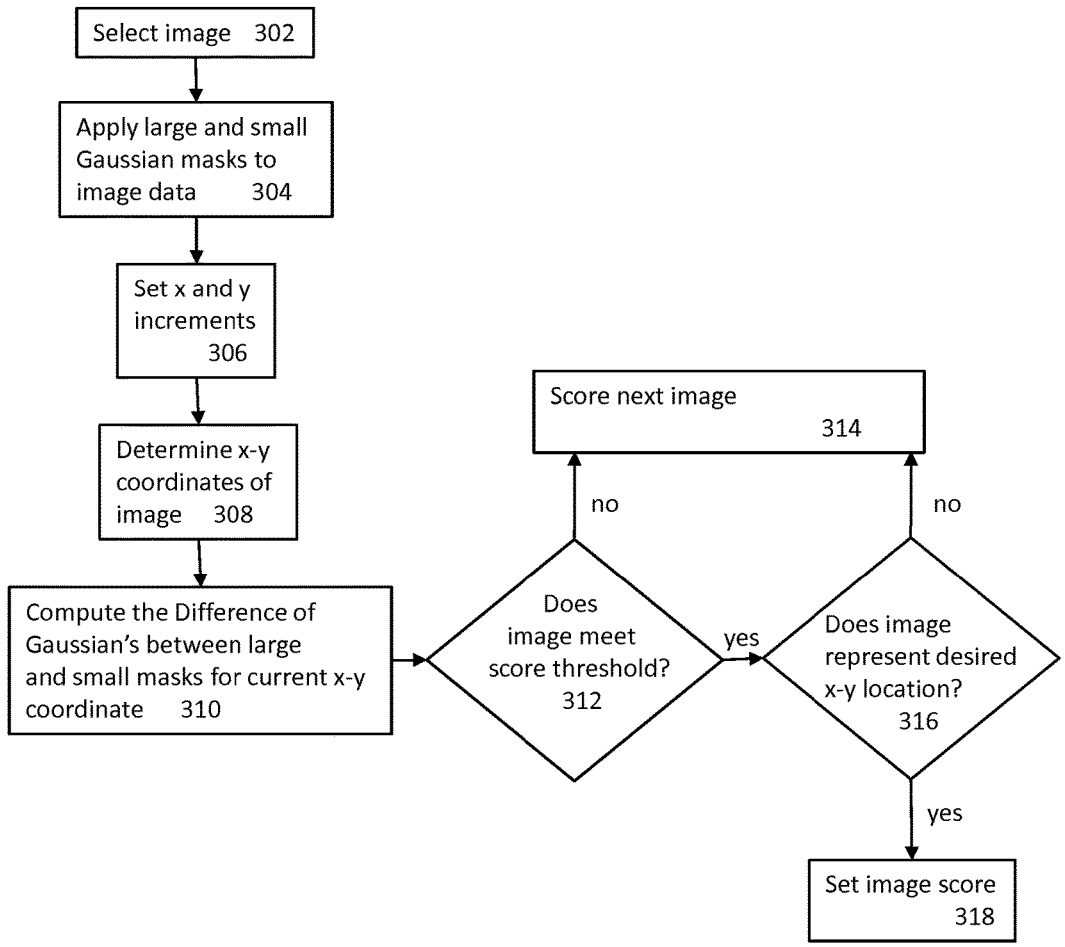
FIG. 3 is a flowchart representation of a disclosed method.

FIG. 3 is a flowchart diagram showing one of many possible methods of scoring an ocular image. The method of FIG. 3 relies upon feature detection using a Difference of Gaussians algorithm. Other feature detection algorithms could be used to implement the methods and apparatus described herein. A scoring process may be initiated by the selection of an image to be scored (step 302). Many types of scoring or detection algorithms including but not limited to the Difference of Gaussians method will include applying masks to image data (step 304). Accordingly, the method of FIG. 3 includes building large and small Gaussian masks which are suitable for detecting the desired feature type as defined by a selection criteria and for determining image location. It is also necessary to set X and Y mask offset increments at a level sufficient to achieve adequate feature detection, yet large enough to yield adequate image capture frame rates based upon computational constraints, typically processor capacity (step 306).

Upon the application of Gaussian masks to the image data and selection of suitable X and Y increment criteria a determination may be calculated in the processor of the X-Y coordinates of the image (step 308). Thereupon the Difference of Gaussians between the large and small image masks may be computed for the current X-Y coordinate (step 310). The solution of the Difference of Gaussians may be scaled and presented as an initial score. If the image meets a predetermined score threshold (step 312) and the image covers the desired X-Y location (step 316) the image may be selected for further processing (step 110 of FIG. 1). If the image does not meet the score threshold or does not cover the desired X-Y location (or otherwise does not meet the specified selection criteria) the next image may be scored (step 314).

As described above, it may be useful in certain diagnostic situations to compare images of an ocular feature obtained from the same eye at different points in time. This functionality may be useful to properly diagnose progressive ocular diseases and disorders or to verify eye health over time. Representative ocular disorders which progress with the passage of time include, but are not limited to, prenatal retinopathy, diabetes induced retinopathy, various macular degeneration diseases, detached retina and similar ocular diseases or degenerative conditions.

Figure 4:
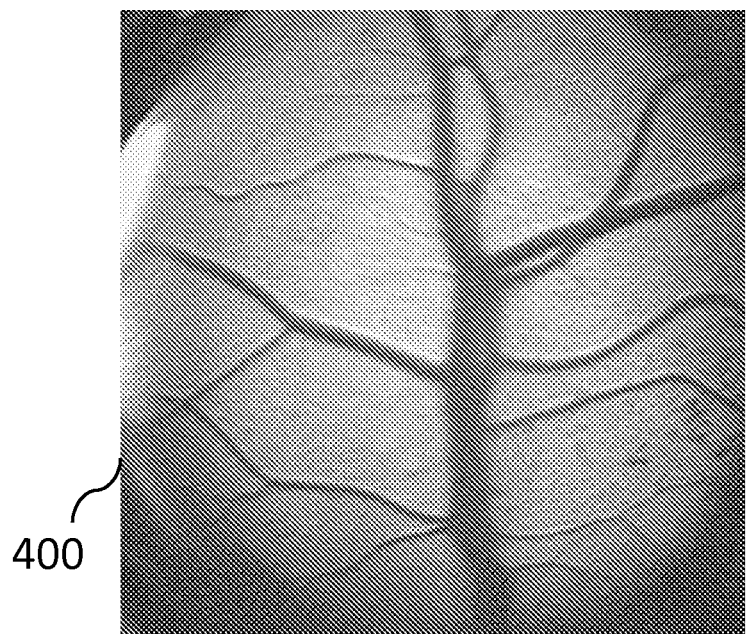
FIG. 4 is a representative image of an ocular feature, namely retinal vasculature.
Figure 6:
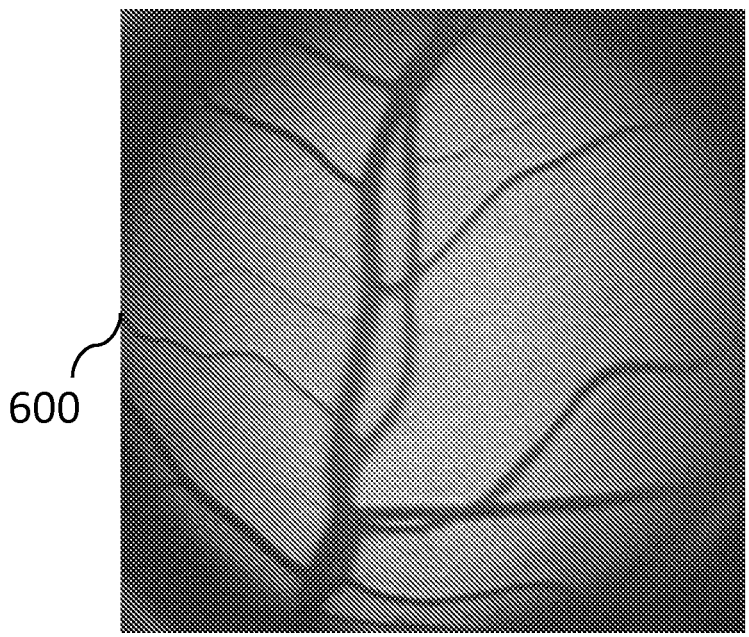
FIG. 6 is a representative image of an ocular feature, namely retinal vasculature, taken at a subsequent point in time from FIG. 4.
Figure 5:
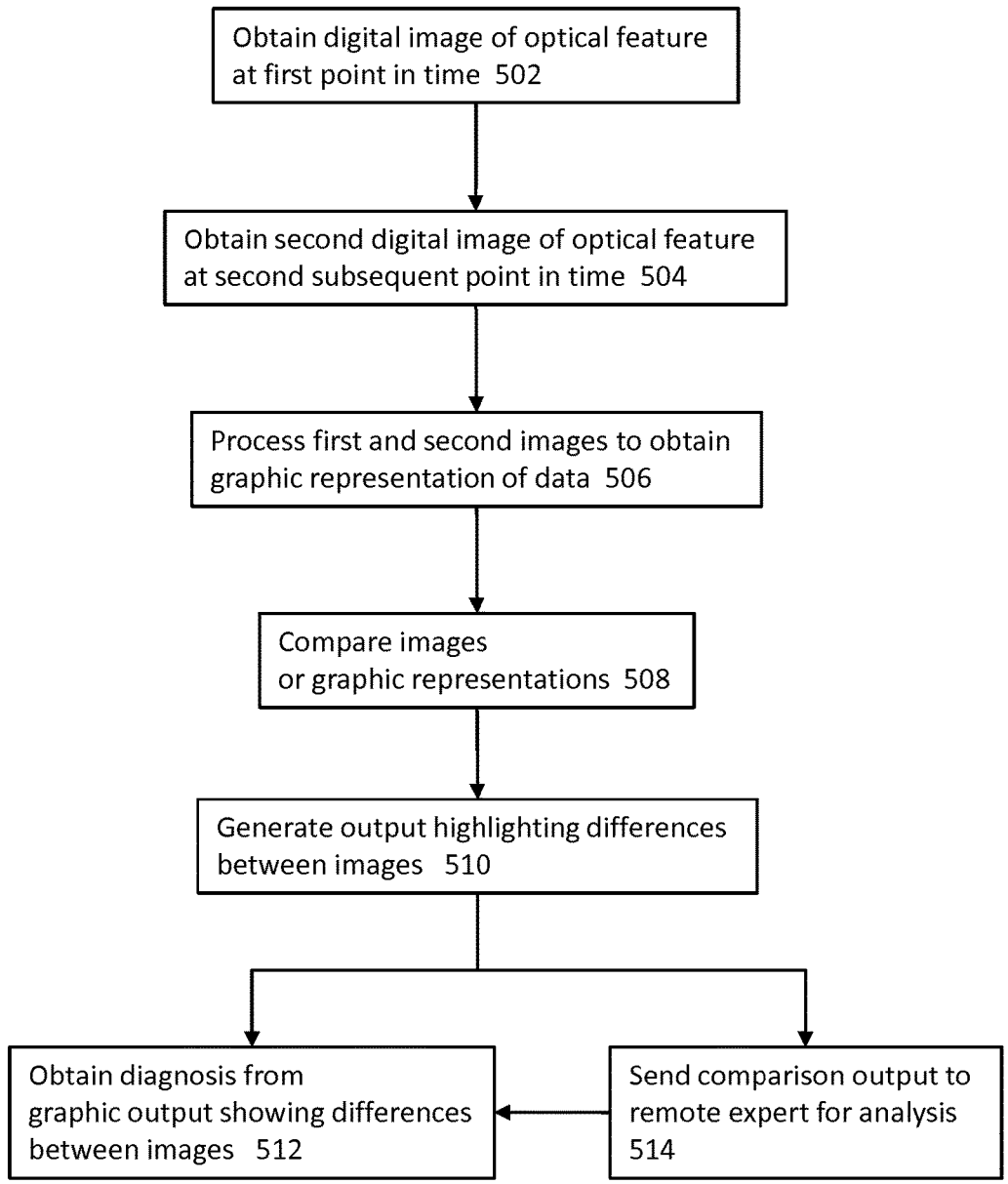
FIG. 5 is a flowchart representation of a disclosed method.

As described above, the apparatus and methods disclosed herein may be used to obtain one or more relatively high quality images of a selected ocular feature. For example, as shown in FIG. 4, an initial image 400 taken at a select point in time may be obtained of the retinal vasculature of a subject eye. (See also step 502 of FIG. 5). Later, after a suitable period of time has passed, a second image 600 of the same ocular feature may be obtained as described above. FIG. 6 is representative of a second image 600 of the retinal vasculature of the subject eye. (See also step 504 of FIG. 5).

Figure 7:
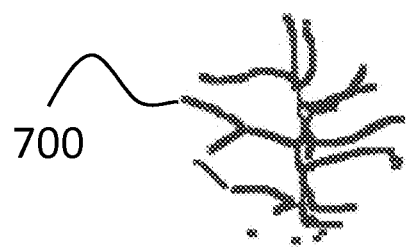
FIG. 7 is a graphic representation of the retinal vasculature data of FIG. 4.
Figure 8:
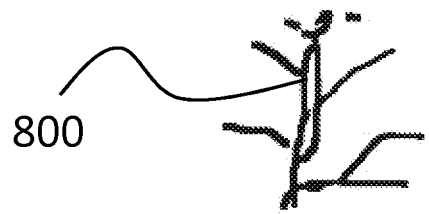
FIG. 8 is a graphic representation of the retinal vasculature data of FIG. 6.

The first and subsequent images of an ocular feature may be directly compared by an expert to make or assist with a diagnosis (Step 508). Alternatively, the autonomous targeting and optical feature identification processes described above may be used to process image data related to the selected ocular feature to create graphic data representations (step 506). See, for example, the vasculature graphics 700, 800 shown in FIGS. 7 and 8 which were extracted as data maps from the images 400 and 600 respectively. Comparison of these graphic representations of optical features using known image comparison techniques can generate a combined output representation having data from both the initial and subsequent images which output highlights one or more differences between the first and subsequent images (step 508). See, for example, the graphic output representation 900 of FIG. 9 where the differences between the graphic representations of FIGS. 7 and 8 are highlighted in a lighter shade, different color or other manner.

Figure 9:
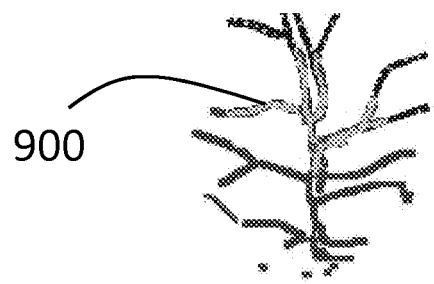
FIG. 9 is a graphic comparison of the data of FIG. 7 and FIG. 8 showing differences.

A graphic map-type output such as illustrated in FIG. 9 is not to be construed as limiting upon the scope of this invention. However, any alternative output should be configured to highlight the differences between the initial and subsequent images of an optical feature. The differences which occur in a subject over time may be indicative of various ocular diseases or conditions. Thus, the methods, apparatus and software described herein may be used to acquire pairs or multiple sets of diagnostic images which may, if desired, be rendered as easily interpreted graphic output autonomously. The output or the original images may then be reviewed by a physician or other highly skilled personnel who was not necessarily present at the time either image was taken. The described embodiments therefore facilitate the rapid and accurate diagnosis of progressive ocular diseases or disorders.

Because the methods described above result in high quality images of selected ocular features plus, optionally, graphic output showing changes to the selected ocular features over time, the apparatus, methods and software described herein facilitate remote diagnosis. For example, a field technician may collect images from a human or animal subject and store the initial images. Later, the first or if desired second images may be transmitted electronically or otherwise to a specialist for analysis and diagnosis (steps 512, 514). Before transmission, the images may be autonomously compared and the resulting output representative of differences between the images may be presented as a graphic or otherwise. The ability to use the disclosed apparatus, methods and software to facilitate remote expert diagnosis is particularly useful in the fields of veterinary medicine or human medical care rendered in remote locations, developing countries or other locations and situations where it is difficult or impossible for each patient to be personally visited by a skilled physician or veterinarian.

The methods and apparatus described herein rely largely upon automated functionality. For example, selected method steps may be implemented autonomously by a processor or processors associated with the apparatus. The scope of the disclosed embodiments includes a computer readable medium having instructions for executing the methods described herein.

It is important to note that while the disclosed embodiments have been described in the context of a fully functioning data processing system, those of ordinary skill in the art will appreciate that the processes and methods described herein are capable of being distributed in the form of a computer readable medium of instructions of a variety of forms and that the scope of the present disclosure includes any particular type of signal bearing media actually used to carry out the distribution. Examples of computer readable media include recordable-type media such as a floppy disk, a hard disk drive, a RAM, and CD-ROMs and transmission-type media such as digital and analog communication links.

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure. In addition, various embodiments disclosed herein can be combined if technically feasible even if disclosed as separate embodiments and such combinations are within the scope of the disclosure and the invention.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A method of obtaining an image of an ocular feature comprising:
    providing a digital video camera;
    providing at least one processor in digital communication with the digital video camera;
    providing an illumination source which is controlled by the processor;
    providing an input source in digital communication with the processor;
    using the input source to define at least one selection criteria related to an anatomical ocular feature of interest, which selection criteria is stored in a memory in digital communication with the processor;
    capturing a first segment of one continuous video stream of sequential ocular images with the digital video camera, wherein the first segment of the one continuous video stream of sequential ocular images is captured at an initial illumination level provided by the illumination source and which illumination level is controlled by the processor;
    processing multiple ocular images of the first segment of the video stream with the processor to score the processed ocular images according to the selection criteria stored in the memory to select an individual ocular image from the first segment of the video stream which selected image is, according to the score determined by the processor, more likely to include the ocular feature of interest than other individual ocular images of the first segment of the video stream; and
    upon selection by the processor of an individual ocular image from the first segment of the video stream more likely to include the ocular feature of interest, controlling the illumination source with the processor to cause the illumination source to provide a second illumination level while capturing a second segment of the video stream of sequential ocular images, wherein the second illumination level is of a higher intensity than the initial illumination level.

2. The method of obtaining an image of an ocular feature of claim 1 further comprising at least one of:
    displaying one or more of the individual ocular images captured during the second segment of the video stream on a display;
    storing one or more of the individual ocular images captured during the second segment of the video stream on a data storage device; and
    electronically transmitting one or more of the individual ocular images captured during the second segment of the video stream.

3. The method of obtaining an image of an ocular feature of claim 1 wherein the initial illumination level is selected to minimize constriction of the pupil of the subject eye.

4. The method of obtaining an image of an ocular feature of claim 3 wherein the duration of the capture of the second segment of the video stream of sequential ocular images is selected to be equal to or less than a constriction response time of the pupil of the subject eye.

5. The method of obtaining an image of an ocular feature of claim 1 wherein the step of defining at least one selection criteria related to an anatomical ocular feature of interest comprises at least one of:
    specifying an ocular feature type; and
    specifying an ocular feature location.

6. The method of obtaining an image of an ocular feature of claim 5 wherein the step of scoring multiple ocular images of the first segment of the video stream with the processor, according to the selection criteria stored in the memory, comprises detecting at least one of an ocular feature and an ocular feature location in the ocular images.

7. The method of obtaining an image of an ocular feature of claim 6 wherein the step of scoring each ocular image of the first segment of the video stream with the processor according to the selection criteria stored in the memory further comprises determining image quality of the ocular images.

8. An apparatus for obtaining an image of an ocular feature comprising:
    a digital video camera;
    a processor in digital communication with the digital video camera;
    an illumination source which is controlled by the processor; and
    an input source in digital communication with the processor, wherein;
        the input source provides for the definition of at least one selection criteria related to an anatomical ocular feature of interest which selection criteria is stored in a memory in digital communication with the processor;
        the digital video camera is controlled by the processor to capture a first segment of one continuous video stream of sequential ocular images, wherein the first segment of the one continuous video stream of sequential ocular images is captured at an initial illumination level provided by the illumination source and which illumination level is controlled by the processor;
        the processor provides for the scoring of multiple ocular images of the first segment of the video stream according to the selection criteria stored in the memory to select an individual ocular images from the first segment of the video stream which image is, according to the score determined by the processor, more likely to include the ocular feature of interest than other individual ocular images of the first segment of the video stream; and wherein, upon selection by the processor of an individual ocular image from the first segment of the video stream more likely to include the ocular feature of interest, the illumination source is controlled with the processor to provide a second illumination level while capturing a second segment of the video stream of sequential ocular images, wherein the second illumination level is of a higher intensity than the initial illumination level.

9. The apparatus for obtaining an image of an ocular feature of claim 8 further comprising at least one of:
a display for displaying one or more of the individual ocular images captured during the second segment of the video stream;
a data storage device for storing one or more of the individual ocular images captured during the second segment of the video stream; and
a communications interface for electronically transmitting one or more of the individual ocular images captured during the second segment of the video stream.

10. The apparatus for obtaining an image of an ocular feature of claim 8 wherein the duration of the capture of the second segment of the video stream of sequential ocular images is selected to be equal to or less than a constriction response time of the pupil of the subject eye.

11. The apparatus for obtaining an image of an ocular feature of claim 8 wherein the input device provides for the definition of at least one selection criteria related to an anatomical ocular feature of interest comprising at least one of:
an ocular feature type; and
an ocular feature location.

12. The apparatus for obtaining an image of an ocular feature of claim 11 wherein processor scores the scored images by detecting at least one of an ocular feature type and an ocular feature location.

13. The apparatus for obtaining an image of an ocular feature of claim 12 wherein the processor scores the scored images by determining image quality.

14. An ocular imaging system, comprising:
a digital video camera;
at least one processor in digital communication with the digital video camera;
an illumination source which is controlled by the processor;
an input source in digital communication with the processor; and
a computer readable medium in communication with the processor, the computer readable medium having encoded thereon a set of instructions executable by the ocular imaging system to perform one or more operations, the set of instructions comprising instructions for:
accepting input from the input source to define at least one selection criteria related to an anatomical ocular feature of interest, which selection criteria is stored in a memory in digital communication with the processor;
capturing a first segment of one continuous video stream of sequential ocular images with the digital video camera, wherein the first segment of the one continuous video stream of sequential ocular images is captured at an initial illumination level provided by the illumination source and which illumination level is controlled by the processor;
processing multiple ocular images of the first segment of the video stream with the processor to score the processed ocular images according to the selection criteria stored in the memory to select an individual ocular image from the first segment of the video stream which image is, according to the score determined by the processor, more likely to include the ocular feature of interest than other individual ocular images of the first segment of the video stream; and
upon selection by the processor of an individual ocular image from the first segment of the video stream more likely to include the ocular feature of interest, controlling the illumination source with the processor to cause the illumination source to provide a second illumination level while capturing a second segment of the video stream of sequential ocular images, wherein the second illumination level is of a higher intensity than the initial illumination level.

15. The ocular imaging system of claim 14 wherein the set of instructions further comprise instructions for:
displaying one or more of the individual ocular images captured during the second segment of the video stream on a display;
storing one or more of the individual ocular images captured during the second segment of the video stream on a data storage device; and
electronically transmitting one or more of the individual ocular images captured during the second segment of the video stream.

16. The ocular imaging system of claim 14 wherein the set of instructions further comprise instructions for selecting the initial illumination level to minimize constriction of the pupil of the subject eye.

17. The ocular imaging system of claim 14 wherein the set of instructions further comprise instructions for selecting the duration of the capture of the second segment of the video stream of sequential ocular images to be equal to or less than a constriction response time of the pupil of the subject eye.

18. The ocular imaging system of claim 14 wherein the set of instructions further comprise instructions for accepting input from the input source to define at least one selection criteria comprising at least one of:
an ocular feature type; and
an ocular feature location.

19. The ocular imaging system of claim 14 wherein the set of instructions further comprises instructions for causing the processor to score a processed image by detecting at least one of an ocular feature location and an ocular feature type.

20. The ocular imaging system of claim 14 wherein the set of instructions further comprise instructions for causing the processor to score a processed image by determining image quality.

* * * * *